(12) United States Patent
Park et al.

(10) Patent No.: US 8,828,011 B2
(45) Date of Patent: Sep. 9, 2014

(54) ARTHROPLASTY DEVICES AND RELATED METHODS

(71) Applicant: OtisMed Corporation, Alameda, CA (US)

(72) Inventors: Ilwhan Park, Walnut Creek, CA (US); Charlie W. Chi, San Francisco, CA (US)

(73) Assignee: OtisMed Corporation, Alameda, CA (US)

( * ) Notice: Subject to any disclaimer, the term of this patent is extended or adjusted under 35 U.S.C. 154(b) by 0 days.

(21) Appl. No.: 13/730,467

(22) Filed: Dec. 28, 2012

(65) Prior Publication Data
US 2013/0116697 A1 May 9, 2013

Related U.S. Application Data

(62) Division of application No. 11/641,382, filed on Dec. 18, 2006, now Pat. No. 8,460,302.

(51) Int. Cl.
| | |
|---|---|
| A61B 17/17 | (2006.01) |
| A61B 17/88 | (2006.01) |
| A61B 17/15 | (2006.01) |
| A61B 17/00 | (2006.01) |

(52) U.S. Cl.
CPC .............. *A61B 17/17* (2013.01); *A61B 17/155* (2013.01); *A61B 17/157* (2013.01); *A61B 2017/00526* (2013.01); *A61B 17/8863* (2013.01)
USPC .......................................................... 606/87

(58) Field of Classification Search
USPC ........ 606/86 R, 87–89; 409/2, 3, 6, 7, 79, 80, 409/175, 219, 227, 289, 291, 292; 700/98
See application file for complete search history.

(56) References Cited

U.S. PATENT DOCUMENTS

| | | | |
|---|---|---|---|
| 4,517,969 | A | 5/1985 | Halcomb et al. |
| 5,098,436 | A | 3/1992 | Ferrante et al. |
| 5,298,254 | A | 3/1994 | Prewett et al. |
| 5,916,221 | A | 6/1999 | Hodorek et al. |

(Continued)

FOREIGN PATENT DOCUMENTS

| | | |
|---|---|---|
| JP | 10-94538 | 4/1998 |
| JP | 2001-092950 | 4/2001 |
| WO | WO 00/35346 | 6/2000 |
| WO | WO 2007/097853 A2 | 8/2007 |

OTHER PUBLICATIONS

U.S. Appl. No. 13/749,095, filed Jan. 24, 2013, Song.
U.S. Appl. No. 13/960,498, filed Aug. 6, 2013, Song.

(Continued)

*Primary Examiner* — Christopher Beccia
(74) *Attorney, Agent, or Firm* — Polsinelli PC (57) ABSTRACT

Methods and apparatuses for forming customized arthroplasty jigs are disclosed. Some of the apparatuses may comprise a plurality of rapid production machines and an automated mechanical system. The automated mechanical system may be configured to transport a first arthroplasty jig blank to a first rapid production machine and a second arthroplasty jig blank to a second rapid production machine. The first rapid production machine may be configured to form a first arthroplasty jig from the first arthroplasty jig blank, and the second rapid production machine may be configured to form a second arthroplasty jig from the second arthroplasty jig blank, the second arthroplasty jig having a different configuration from the first arthroplasty jig.

26 Claims, 9 Drawing Sheets

(56) References Cited

U.S. PATENT DOCUMENTS

| | | | |
|---|---|---|---|
| 6,772,026 B2* | 8/2004 | Bradbury et al. ............... 700/98 |
| 6,799,066 B2 | 9/2004 | Steines et al. |
| 7,715,602 B2 | 5/2010 | Richard |
| 8,115,485 B1 | 2/2012 | Maier et al. |
| 8,170,716 B2 | 5/2012 | Coste-Maniere et al. |
| 8,460,303 B2 | 6/2013 | Park |
| 8,480,679 B2 | 7/2013 | Park |
| 8,483,469 B2 | 7/2013 | Pavlovskaia et al. |
| D691,719 S | 10/2013 | Park |
| 8,545,509 B2 | 10/2013 | Park et al. |
| 2004/0146369 A1* | 7/2004 | Kato ............................ 409/219 |
| 2005/0054914 A1 | 3/2005 | Duerk et al. |
| 2005/0080426 A1 | 4/2005 | Qian |
| 2005/0272998 A1 | 12/2005 | Diehl et al. |
| 2006/0079755 A1 | 4/2006 | Stazzone et al. |
| 2006/0244448 A1 | 11/2006 | Ballon et al. |
| 2007/0010732 A1 | 1/2007 | DeYoe et al. |
| 2007/0100338 A1 | 5/2007 | Deffenbaugh et al. |
| 2007/0123856 A1 | 5/2007 | Deffenbaugh et al. |
| 2007/0123857 A1 | 5/2007 | Deffenbaugh et al. |
| 2008/0089591 A1 | 4/2008 | Zhou et al. |
| 2011/0071537 A1 | 3/2011 | Koga et al. |
| 2013/0115474 A1 | 5/2013 | Park |
| 2013/0123789 A1 | 5/2013 | Park |
| 2013/0190767 A1 | 7/2013 | Park et al. |
| 2013/0345845 A1 | 12/2013 | Park et al. |
| 2014/0005997 A1 | 1/2014 | Park |
| 2014/0078139 A1 | 3/2014 | Park et al. |
| 2014/0081277 A1 | 3/2014 | Park et al. |

OTHER PUBLICATIONS

U.S. Appl. No. 14/086,878, filed Nov. 21, 2013, Park et al.
Amendment Under 37 C.F.R. 1.312, U.S. Appl. No. 13/374,960, filed May 7, 2013, 6 pages.
Audette et al. "An algorithmic overview of surface registration techniques for medical imaging." Medical Image Analysis, vol. 4, No. 3, Sep. 1, 2000, pp. 201-217.
European Search Report, EP09739422.5, dated Mar. 28, 2013, 9 pages.
Final Office Action, U.S. Appl. No. 12/636,939, mailed Jan. 25, 2013, 9 pages.
Final Office Action, U.S. Appl. No. 11/641,569, dated Nov. 29, 2013, 20 pages.
Final Office Action, U.S. Appl. No. 12/390,667, dated Oct. 25, 2013, 17 pages.
Final Office Action, U.S. Appl. No. 12/505,056, dated Dec. 30, 2013, 48 pages.
Final Office Action, U.S. Appl. No. 12/546,545, dated Oct. 7, 2013, 24 pages.
Final Office Action, U.S. Appl. No. 13/723,904, dated Dec. 24, 2013, 10 pages.
Final Office Action, U.S. Appl. No. 13/730,585, dated Dec. 27, 2013, 8 pages.
Ibáñz et al., The ITK Software Guide, Second Edition, Updated for ITK version 2.4, Nov. 21, 2005, pp. 114, 396-411, and 426.
Japanese Office Action, JP Application No. 2011-507530, dated Dec. 17, 2013, 8 pages.
Non-Final Office Action, U.S. Appl. No. 11/641,569, mailed Jul. 12, 2013, 21 pages.
Non-Final Office Action, U.S. Appl. No. 11/642,385, dated Oct. 22, 2013, 37 pages.
Non-Final Office Action, U.S. Appl. No. 11/656,323, dated Oct. 22, 2013, 36 pages.
Non-Final Office Action, U.S. Appl. No. 11/946,002, dated Oct. 2, 2013, 39 pages.
Non-Final Office Action, U.S. Appl. No. 11/946,002, dated Feb. 6, 2014, 46 pages.
Non-Final Office Action, U.S. Appl. No. 12/390,667, mailed May 8, 2013, 20 pages.
Non-Final Office Action, U.S. Appl. No. 12/505,056, mailed Jun. 28, 2013, 7 pages.
Non-Final Office Action, U.S. Appl. No. 12/636,939, mailed Apr. 25, 2013, 16 pages.
Non-Final Office Action, U.S. Appl. No. 12/760,388, mailed Jun. 20, 2013, 54 pages.
Non-Final Office Action, U.S. Appl. No. 13/723,904, mailed Aug. 9, 2013, 6 pages.
Non-Final Office Action, U.S. Appl. No. 13/730,585, mailed Jun. 11, 2013, 10 pages.
Non-Final Office Action, U.S. Appl. No. 13/730,608, dated Oct. 7, 2013, 10 pages.
Notice of Allowance, Design U.S. Appl. No. 29/394,882, mailed May 24, 2013, 16 pages.
Notice of Allowance, U.S. Appl. No. 11/641,569, dated Feb. 5, 2014, 11 pages.
Notice of Allowance, U.S. Appl. No. 12/390,667, dated Jan. 17, 2014, 9 pages.
Notice of Allowance, U.S. Appl. No. 12/505,056, dated Mar. 6, 2014, 10 pages.
Notice of Allowance, U.S. Appl. No. 12/546,545, dated Dec. 26, 2013, 9 pages.
Notice of Allowance, U.S. Appl. No. 12/563,809, mailed May 28, 2013, 11 pages.
Notice of Allowance, U.S. Appl. No. 12/636,939, dated Oct. 7, 2013, 28 pages.
Notice of Allowance, U.S. Appl. No. 12/760,388, dated Jan. 22, 2014, 13 pages.
Notice of Allowance, U.S. Appl. No. 13/086,275, mailed Aug. 27, 2013, 31 pages.
Notice of Allowance, U.S. Appl. No. 13/374,960, mailed May 6, 2013, 20 pages.
Notice of Allowance, U.S. Appl. No. 13/723,904, dated Mar. 7, 2014, 8 pages.
Notice of Allowance, U.S. Appl. No. 13/730,585, dated Mar. 18, 2014, 10 pages.
Preliminary Amendment, U.S. Appl. No. 13/731,697, filed May 10, 2013, 6 pages.
Preliminary Amendment, U.S. Appl. No. 13/731,850, filed Apr. 11, 2014, 8 pages.
Response to Final Office Action, U.S. Appl. No. 11/641,569, dated Jan. 29, 2014, 10 pages.
Response to Final Office Action, U.S. Appl. No. 12/390,667, dated Dec. 23, 2013, 5 pages.
Response to Final Office Action, U.S. Appl. No. 12/563,809, filed May 6, 2013, 15 pages.
Response to Final Office Action, U.S. Appl. No. 12/546,545, dated Dec. 9, 2013, 8 pages.
Response to Final Office Action, U.S. Appl. No. 12/505,056, dated Feb. 26, 2014, 19 pages.
Response to Final Office Action, U.S. Appl. No. 13/723,904, dated Feb. 19, 2014, 7 pages.
Response to Final Office Action, U.S. Appl. No. 13/730,585, dated Feb. 26, 2014, 9 pages.
Response to Non-Final Office Action, U.S. Appl. No. 13/086,275, filed May 7, 2013, 11 pages.
Response to Non-Final Office Action, U.S. Appl. No. 12/546,545, filed Jul. 15, 2013, 14 pages.
Response to Non-Final Office Action, U.S. Appl. No. 12/636,939, filed Jul. 16, 2013, 15 pages.
Response to Non-Final Office Action, U.S. Appl. No. 12/390,667, filed Aug. 7, 2013, 22 pages.
Response to Non-Final Office Action, U.S. Appl. No. 12/760,388, filed Sep. 12, 2013, 15 pages.
Response to Non-Final Office Action, U.S. Appl. No. 12/505,056, filed Oct. 9, 2013, 17 pages.
Response to Non-Final Office Action, U.S. Appl. No. 13/730,585, filed Oct. 9, 2013, 15 pages.
Response to Non-Final Office Action, U.S. Appl. No. 11/641,569, filed Oct. 11, 2013, 12 pages.
Response to Non-Final Office Action, U.S. Appl. No. 13/723,904, filed Nov. 6, 2013, 8 pages.

(56) References Cited

OTHER PUBLICATIONS

Response to Non-Final Office Action, U.S. Appl. No. 11/946,002, filed Dec. 6, 2013, 18 pages.
Response to Non-Final Office Action, U.S. Appl. No. 13/730,608, dated Jan. 7, 2014, 16 pages.
Response to Non-Final Office Action, U.S. Appl. No. 11/656,323, dated Jan. 17, 2014, 10 pages.
Response to Non-Final Office Action, U.S. Appl. No. 11/642,385, dated Feb. 24, 2014, 16 pages.
Restriction Requirement, U.S. Appl. No. 13/488,505, dated Mar. 4, 2014, 5 pages.
Siemens MAGNETOM Sonata 1.5T Technical Specifications, pp. 1-4, accessed online Jan. 28, 2014.
Supplementary European Search Report and Opinion, EP 09739474.6, dated Feb. 27, 2014, 7 pages.
Xie et al. "Segmentation by surface-to-image registration." proceedings of SPIE, vol. 6144, Mar. 2 2006, pp. 614405-1-614405-7.

* cited by examiner

ARTHROPLASTY DEVICES AND RELATED METHODS

CROSS-REFERENCE TO RELATED APPLICATIONS

This present application is a divisional application of U.S. application Ser. No. 11/641,382 filed Dec. 18, 2006, which application is incorporated by reference herein for all that it discloses or teaches.

TECHNICAL FIELD

The methods and apparatuses described herein relate generally to the field of implants, as well as jigs that may be used to assist in positioning implants at a target site. More specifically, the methods and apparatuses described herein relate to the field of rapid production of high volumes of arthroplasty jigs and/or arthroplasty implants.

BACKGROUND

Over time and through repeated use, bones and joints can become damaged or worn. For example, repetitive strain on bones and joints (e.g., through athletic activity), traumatic events, and certain diseases (e.g., arthritis) can cause cartilage in joint areas to wear down. As a result, fluid can accumulate in these joint areas, resulting in pain, stiffness, and decreased mobility.

Arthroplasty procedures can be used to repair damaged joints. During a typical arthroplasty procedure, an arthritic or otherwise dysfunctional joint can be remodeled or realigned, or an implant can be implanted into the damaged region. Arthroplasty procedures may take place in any of a number of different regions of the body, such as a knee, a hip, a shoulder, or an elbow.

As mentioned above, during some arthroplasty procedures, an implant may be implanted into the damaged region. The implant may provide support and structure to the damaged region, and may help to restore the damaged region, thereby enhancing its functionality. Prior to implantation of the implant in the damaged region, the damaged region can be prepared to receive the implant. For example, in a knee arthroplasty procedure, one or more of the bones in the knee area, such as the femur and/or the tibia, may be treated (e.g., cut, drilled, reamed, and/or resurfaced) to provide one or more surfaces that can align with the implant and thereby accommodate the implant.

Prior to treating any regions of a bone, it is important to correctly determine the location at which the treatment will take place. In some methods, an arthroplasty jig may be used to accurately position a finishing instrument, such as a cutting, drilling, reaming, or resurfacing instrument. The arthroplasty jig may, for example, include one or more apertures and/or slots that are configured to accept such an instrument. In certain variations, an arthroplasty jig may be customized to correspond to a particular patient's anatomy. For example, while individual human knees share some characteristics, they also can differ from each other in certain ways. As an example, knee alignment (e.g., valgus and varus) can vary from patient to patient. The use of a customized arthroplasty jig may enhance the precision of any cuts or other modifications that are made to a damaged region, such as a damaged knee region, during surgery to repair or restore the damaged region. For at least these reasons, customized arthroplasty jigs can provide for an effective and efficient arthroplasty procedure.

A relatively high number of knee replacement surgeries are conducted each year, and the total number of knee replacement surgeries is expect to continue to grow. For example, it is estimated that approximately 500,000 knee replacement surgeries were performed in the United States in 2005, and it is projected that approximately 1,370,000 knee replacement surgeries will be performed in the United States in 2030. Accordingly, it would be desirable to manufacture a relatively high volume of customized arthroplasty jigs in a relatively short period of time, to be able to meet the demand for quality products. It would also be desirable to economically manufacture a relatively high volume of customized arthroplasty jigs.

BRIEF SUMMARY

Described here are methods and apparatuses that may be used to manufacture a relatively high volume of customized arthroplasty jigs in a relatively short period of time. Certain of the apparatuses described here include an automated mechanical system and at least one rapid production machine, such as a plurality of rapid production machines. Some of the methods described here generally comprise activating the automated mechanical system so that it transports an arthroplasty jig blank to a rapid production machine that is configured to form an arthroplasty jig from the arthroplasty jig blank. After transporting the first arthroplasty jig blank, the automated mechanical system transports another arthroplasty jig blank to another component of the same rapid production machine, or to another rapid production machine. The second component or second rapid production machine also is configured to form an arthroplasty jig from the arthroplasty jig blank. The arthroplasty jigs that are formed by the two different components of the same rapid production machine, or by the two different rapid production machines, have different configurations. Thus, the apparatus and method may be used to produce multiple different customized arthroplasty jigs.

The method can be repeated as desired, so that the automated mechanical system continues to bring arthroplasty jig blanks to the rapid production machine or machines. As the arthroplasty jigs are formed, the automated mechanical system can remove the arthroplasty jigs from the rapid production machines, and transport them to another location, such as a temporary storage site. During operation, the automated mechanical system may be in communication with a computer that provides the automated mechanical system with machining instructions for each arthroplasty jig blank that is transported to a rapid production machine. Each machining instruction can be unique to the particular anatomy of a patient, and thus can result in the production of an arthroplasty jig that is customized to that patient.

Certain variations of the apparatuses may be configured to produce at least 30 customized arthroplasty jigs per hour, at least 50 customized arthroplasty jigs per hour, or at least 100 customized arthroplasty jigs per hour. Some variations of the apparatuses may include at least one rapid production machine that is configured to produce one customized arthroplasty jig every three minutes, five minutes, or ten minutes. The rapid production machines and the apparatuses generally may be able to produce customized arthroplasty jigs at a relatively high rate. Thus, the current high demand and projected future high demand for customized arthroplasty jigs may be satisfied, without resulting in a sacrifice in quality.

The rapid production machines may be, for example, computer numerical control (CNC) machines or stereo-lithograph (SLA) machines, or a combination thereof. In some variations in which the rapid production machines include CNC machines, one or more of the CNC machines may be a four-axis CNC machine or a five-axis CNC machine. Some variations of the apparatuses may include two or more rapid production machines, such as four, five, six, eight, or ten rapid production machines. Furthermore, the rapid production machines may be arranged in any of a number of different ways. For example, the rapid production machines may be arranged to form one or more rows, or may be arranged in a generally circular formation. In certain variations, the rapid production machines may be arranged in such a way as to form one or more spaces through which the automated mechanical system can enter and/or exit.

The automated mechanical system may be configured to remove an arthroplasty jig from a rapid production machine once the formation of the arthroplasty jig has been completed. The automated mechanical system may further be configured to transport the completed arthroplasty jig from the rapid production machine to a station or site. The station or site may, for example, be configured to clean and/or package the arthroplasty jigs, or to store the arthroplasty jigs.

The automated mechanical system may transport the arthroplasty jig blanks and the arthroplasty jigs in any selected order. As an example, the automated mechanical system may transport a first arthroplasty jig blank to a first rapid production machine, and then may transport a second arthroplasty jig blank to a second rapid production machine. Thereafter, the automated mechanical system may remove the completed arthroplasty jig from the first rapid production machine and transport it to a cleaning and packaging station. Alternatively, the automated mechanical system may transport a third arthroplasty jig blank to a third rapid production machine. The order in which the automated mechanical system operates can be selected as desired.

DETAILED DESCRIPTION

Described here are methods and apparatuses for manufacturing a plurality of customized arthroplasty jigs. It should be understood from the outset that while methods of making customized knee arthroplasty jigs are described in detail here, the methods may be used, and are contemplated for use, in making any type of arthroplasty jigs, including, for example, arthroplasty jigs that are suited for use in the hip, shoulder, or elbow.

In general, the methods include using an apparatus comprising an automated mechanical system and at least one rapid production machine that forms the customized arthroplasty jigs. In some variations, the apparatus may include multiple rapid production machines. The automated mechanical system can deliver arthroplasty jig blanks to the rapid production machine or machines, and can communicate machining instructions from a computer to the rapid production machine or machines. Upon receiving machining instructions from the automated mechanical system, a rapid production machine can machine an arthroplasty jig blank to form a customized arthroplasty jig according to the instructions. The automated mechanical system can also remove completed arthroplasty jigs from the rapid production machine or machines, thereby freeing the rapid production machine or machines to form additional arthroplasty jigs. In some variations, the automated mechanical system can transport completed arthroplasty jigs to other stations or sites of the apparatus, such as a finishing station that can clean and/or package the completed arthroplasty jigs. This use of the automated mechanical system and the rapid production machine or machines may result in the relatively efficient and productive manufacture of customized arthroplasty jigs.

Figure 1:
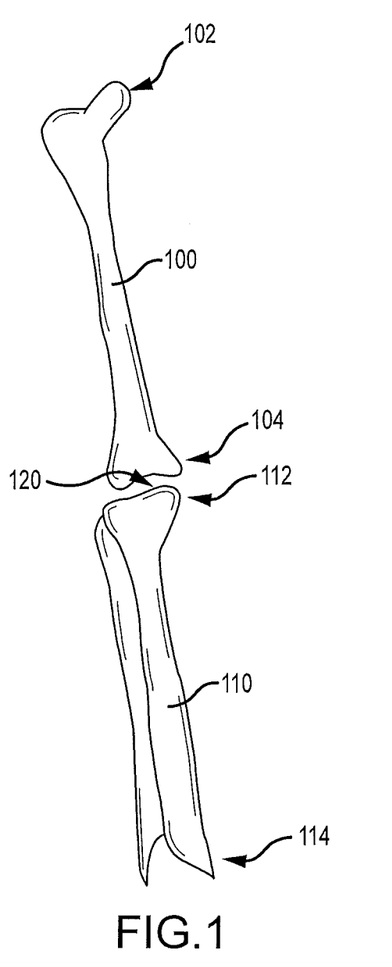
FIG. 1 is an illustration of leg bones of a subject.

Turning now to the figures, FIG. 1 is an illustration of the leg bones of a human subject. As shown in FIG. 1, the leg bones include a femur (100) having an anterior end (102) and a posterior end (104), and a tibia (110) having an anterior end (112) and a posterior end (114). A joint (120) is formed between femur (100) and tibia (110), and may, as a result of damage or wear, require repair or restoration using, for example, an arthroplasty procedure.

As discussed above, in some variations of an arthroplasty procedure, one or more arthroplasty jigs may be employed to help prepare the damaged region for an implant. The arthroplasty jigs may be used, for example, to aid in the correct placement of finishing instruments, such as cutting, drilling, reaming, and resurfacing instruments.

As an example, some arthroplasty methods may include using an arthroplasty jig to accurately position a reciprocating saw blade. The reciprocating saw blade may be used, for example, to cut the damaged bone region to provide one or more planar surfaces. The planar surfaces may assist in the alignment and positioning of an implant at a target site in the damaged bone region. Arthroplasty jigs may also be used, for example, to position one or more pins that secure an implant to a target site in the damaged bone region.

Figure 2A:
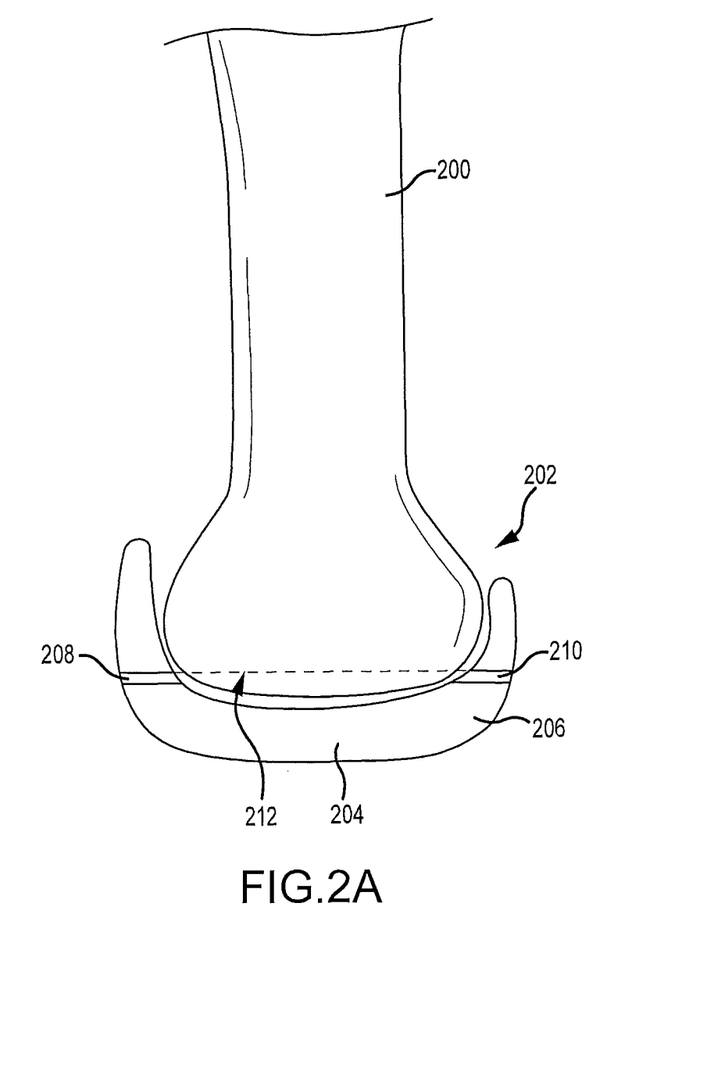
FIG. 2A is an illustration of a portion of a femur of a subject, and an arthroplasty jig engaged with the portion of the femur.
Figure 2B:
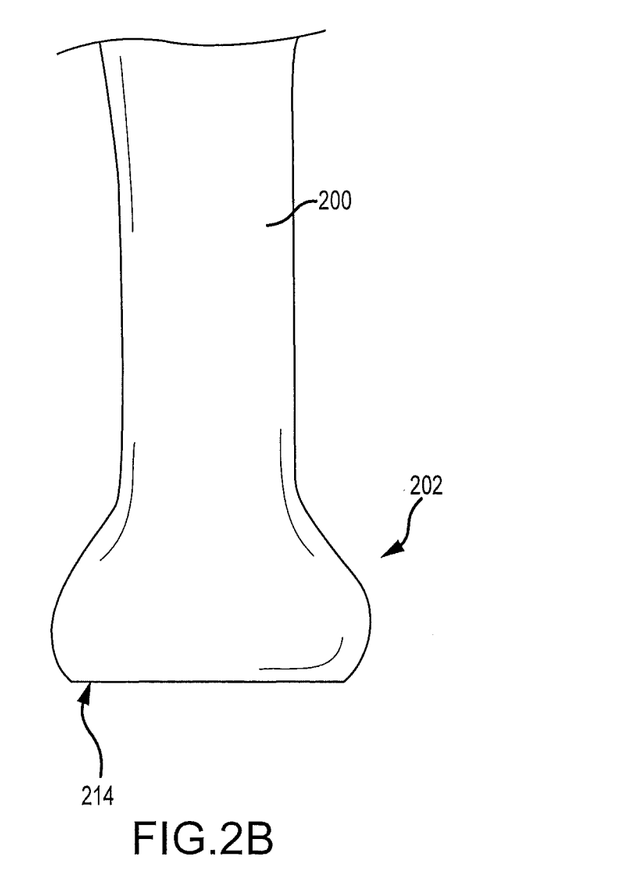
FIG. 2B is an illustration of the portion of the femur of FIG. 2A, after the portion has been cut using a cutting instrument.

An exemplary femoral arthroplasty jig is shown in FIG. 2A. As shown in FIG. 2A, a femur (200) has a posterior end (202). An arthroplasty jig (204) is aligned with posterior end (202), and has a body (206) including two slots (208) and (210). Slots (208) and (210) can be used, for example, to position a cutting instrument (e.g., a reciprocating saw blade). The cutting instrument, in turn, can be used to form a cut (212) that removes a portion of posterior end (202) of femur (200). The result, as shown in FIG. 2B, is a planar surface (214) along posterior end (202) of femur (200). Planar surface (214) may, for example, align with a corresponding planar surface of an implant that is implanted into a damaged region of the knee that is at least partially defined by femur (200).

Figure 3A:
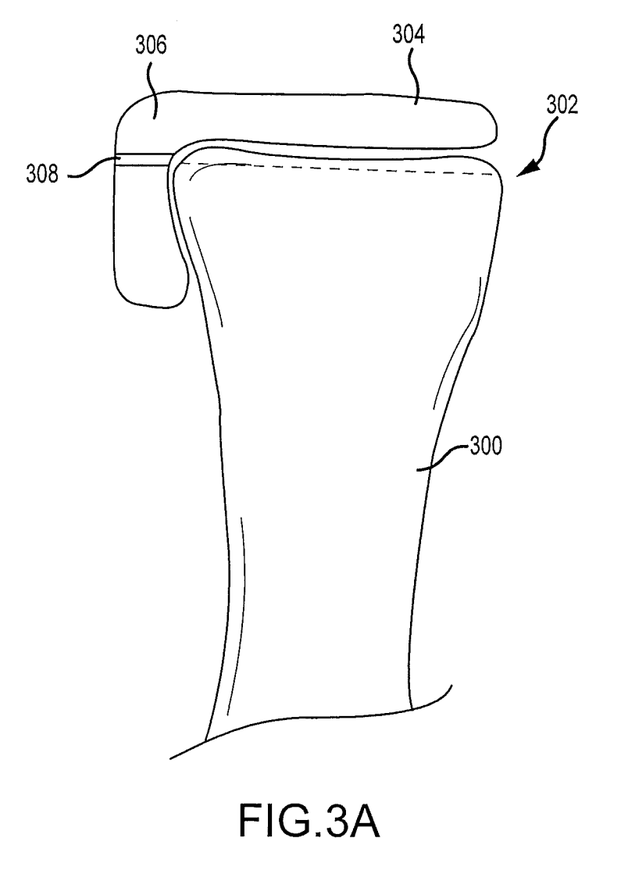
FIG. 3A is an illustration of a portion of a tibia of a subject, and an arthroplasty jig engaged with the portion of the tibia.
Figure 3B:
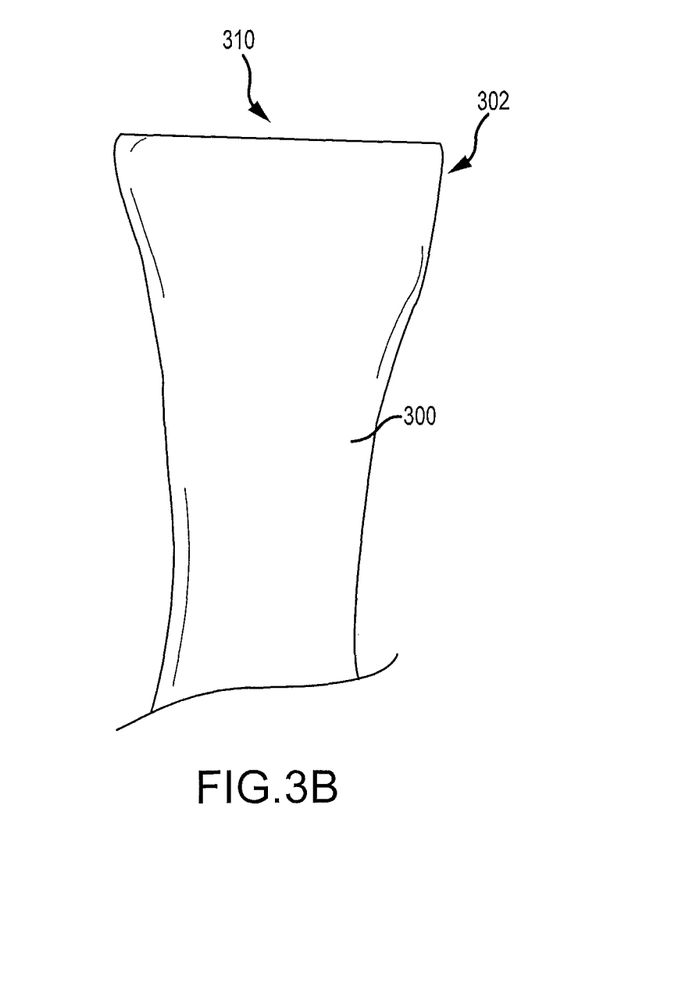
FIG. 3B is an illustration of the portion of the tibia of FIG. 3A, after the portion has been cut using a cutting instrument.

Similarly, an exemplary tibial arthroplasty jig is shown in FIG. 3A. As shown in FIG. 3A, a tibia (300) has an anterior end (302). An arthroplasty jig (304) is aligned with anterior end (302), and has a body (306) including a slot (308). Slot (308) can be used for placement of a cutting instrument (e.g., a reciprocating saw blade). The cutting instrument can be used, for example, to form a cut that removes a portion of anterior end (302) of tibia (300). The result, as shown in FIG.

3B, is a planar surface (310) along anterior end (302) of tibia (300). Planar surface (310) may, for example, align with a corresponding planar surface of an implant that is implanted into a damaged region of the knee that is at least partially defined by tibia (300).

As discussed above, arthroplasty jigs may be customized so that the accuracy of their positioning (and, therefore, the accuracy with which they position finishing instruments) can be enhanced. Various methods may be used to form customized arthroplasty jigs, such as the methods described, for example, in U.S. patent application Ser. No. 10/146,862, filed on May 15, 2002, which is hereby incorporated by reference in its entirety.

Figure 4:
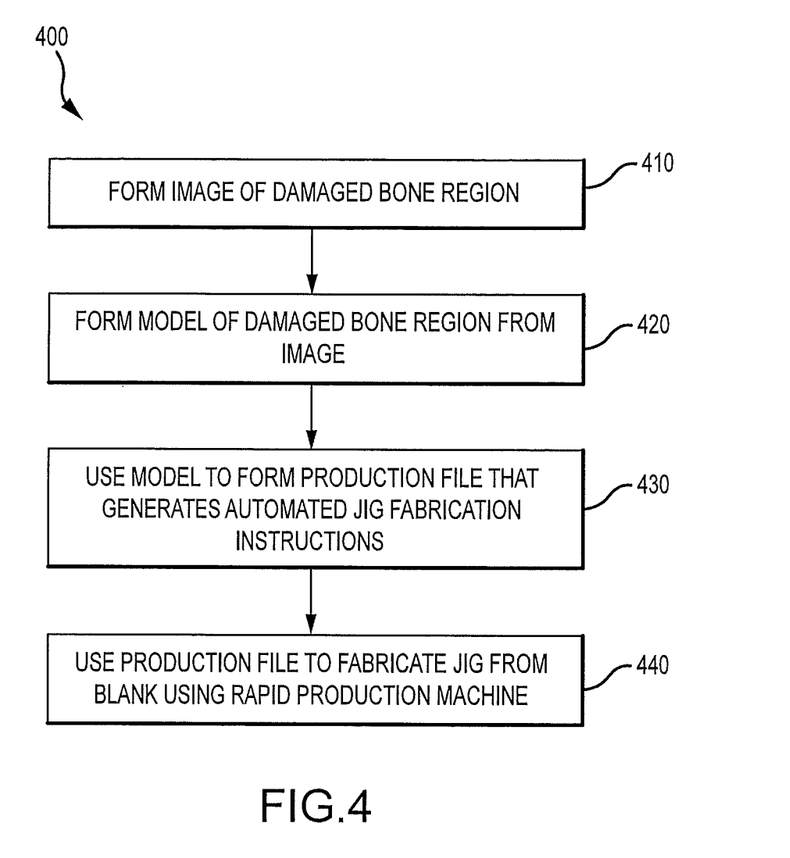
FIG. 4 is a flowchart representation of a method of treating a damaged bone region of a subject.

One variation of a method (400) that may be used to form customized arthroplasty jigs is depicted as a flowchart in FIG. 4. As shown in FIG. 4, this illustrative method comprises forming an image of a damaged bone region of a patient (410) using, for example, computer tomography (CT) and/or magnetic resonance imaging (MRI). The image may be formed specifically of the damaged bone region, or may include portions of the bone that are not damaged. As an example, an image of a damaged knee region may include the entirety of the knee region, as well as the entirety of the associated femur and tibia. After the image has been formed, a three-dimensional model of the damaged bone region is formed from the image (420). The model may be formed, for example, by using the image to determine location coordinate values of each of a sequence of spaced apart surface points in the damaged bone region, and then using a mathematical model to estimate or compute the three-dimensional model. Thereafter, the model and the image are used to generate a production file that provides automated arthroplasty jig fabrication instructions (430) to a rapid production machine, which fabricates a customized arthroplasty jig from an arthroplasty jig blank according to the instructions (440).

Customized arthroplasty jigs may provide many advantages. A hospital that uses customized arthroplasty jigs may be able to maintain a relatively low inventory of the arthroplasty jigs, because the arthroplasty jigs can be provided to the hospital on an as-needed basis, and are customized to particular patients. Accordingly, the hospital may not need to maintain multiple arthroplasty jigs of different sizes and shapes in inventory. Similarly, the use of customized arthroplasty jigs may lead to a decrease in the total number of operating tools required to be in the operating room. Furthermore, customized arthroplasty jigs may provide for enhanced implant alignment and positioning relative to non-customized arthroplasty jigs. This enhanced alignment and positioning may, in turn, decrease the likelihood of follow-up surgery (e.g., to adjust the alignment of the implant), and increase the useful life of the implant. Moreover, patients may experience reduced recovery time when customized arthroplasty jigs are used, in comparison to non-customized arthroplasty jigs. Customized arthroplasty jigs may result in fewer complications during surgery than non-customized arthroplasty jigs, and may allow a damaged bone region to be restored to an earlier, better condition.

Figure 5:
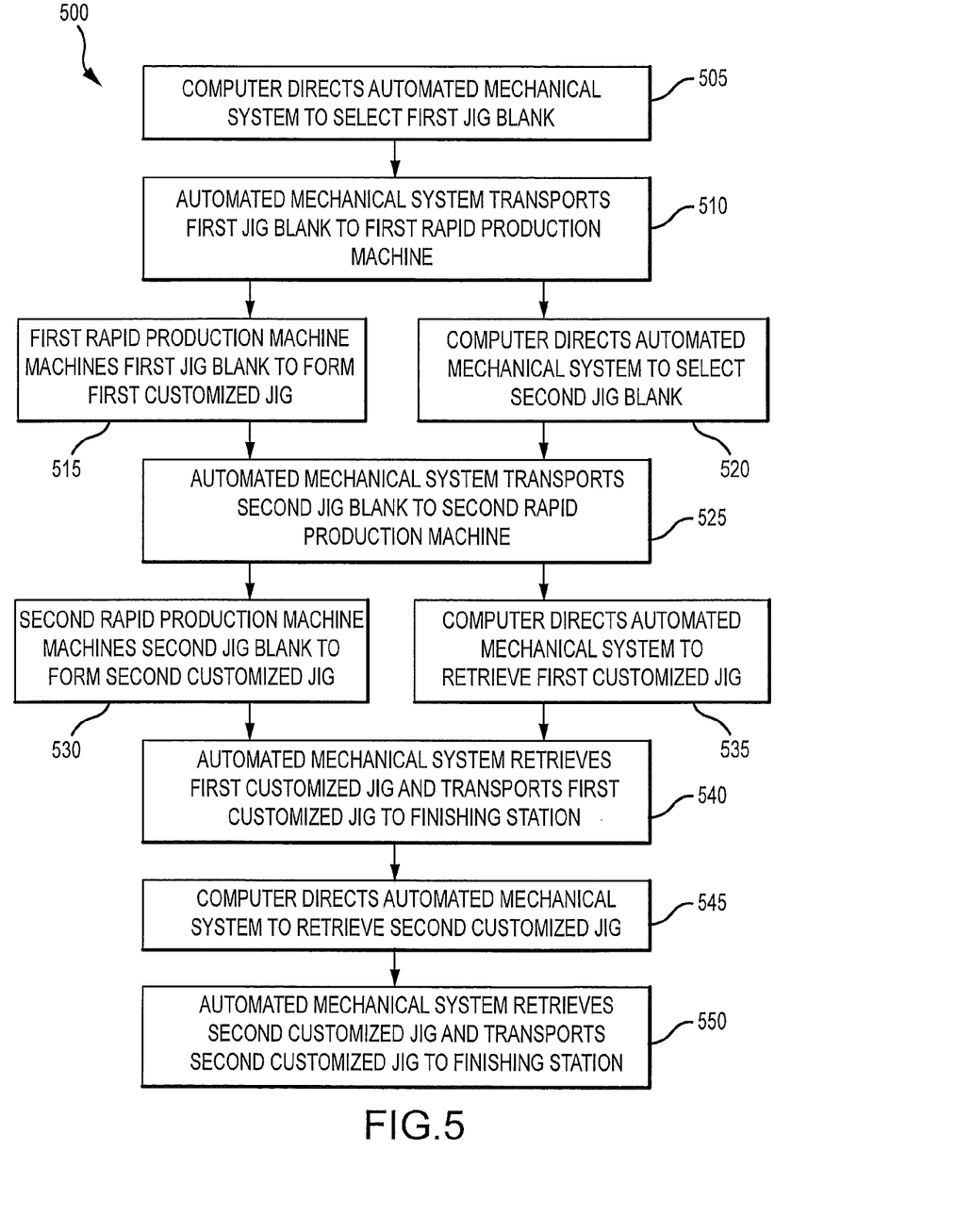
FIG. 5 is a flowchart representation of a method of manufacturing arthroplasty jigs.

At least for the reasons discussed above, it would be desirable to be able to manufacture a relatively high volume of customized arthroplasty jigs in a relatively short period of time. FIG. 5 provides a flowchart representation of one variation of a method (500) that may be used to produce high volumes of customized arthroplasty jigs efficiently.

As shown in FIG. 5, a computer that is in communication with an automated mechanical system directs the automated mechanical system to select a first arthroplasty jig blank (505). After selecting the first arthroplasty jig blank, the automated mechanical system transports the first arthroplasty jig blank to a first rapid production machine (510). The automated mechanical system also communicates customized machining instructions from the computer to the first rapid production machine, so that the first rapid production machine can machine the first arthroplasty jig blank to form a first customized arthroplasty jig (515). The computer then directs the automated mechanical system to select a second arthroplasty jig blank (520), which the automated mechanical system transports to a second rapid production machine (525). The automated mechanical system also communicates customized machining instructions from the computer to the second rapid production machine, so that the second rapid production machine can machine the second arthroplasty jig blank to form a second customized arthroplasty jig (530). The computer then directs the automated mechanical system to retrieve the completed first customized arthroplasty jig (535). Accordingly, the automated mechanical system retrieves the first customized arthroplasty jig and transports the first customized arthroplasty jig to a finishing station (540). Finally, the computer directs the automated mechanical system to retrieve the second customized arthroplasty jig (545). After retrieving the second customized arthroplasty jig, the automated mechanical system transports the second customized arthroplasty jig to the finishing station (550).

The steps in the above-described method (500) can be repeated as desired, to produce any number of customized arthroplasty jigs, such as 100, 500, or 1000 customized arthroplasty jigs. Furthermore, the steps need not be performed in the specific order described with reference to FIG. 5. For example, an automated mechanical system may pick up eight arthroplasty jig blanks and deliver them to eight individual rapid production machines, prior to retrieving any completed customized arthroplasty jigs from the rapid production machines. Additionally, in some variations of the method, an automated mechanical system may transport multiple arthroplasty jig blanks to a single rapid production machine, or may pick up multiple arthroplasty jig blanks at once, and then distribute the arthroplasty jig blanks to individual rapid production machines. Moreover, in certain variations of the method, one or more steps may be omitted. For example, the automated mechanical system may not transport the customized arthroplasty jigs to a finishing station.

In certain variations of the above-described method, an apparatus may be used to manufacture, for example, at least 30 customized arthroplasty jigs per hour, at least 50 customized arthroplasty jigs per hour, or at least 100 customized arthroplasty jigs per hour. Some variations of the apparatuses may include at least one rapid production machine that is configured to produce one customized arthroplasty jig every three minutes, five minutes, or ten minutes. These are just specific examples and are not intended to be limiting; an apparatus may be used to manufacture a lower or higher number of customized arthroplasty jigs per hour, and/or a rapid production machine may be configured to produce an arthroplasty jig in a shorter or longer period of time.

The arthroplasty jigs described herein may be individually packaged, or may be packaged together with other arthroplasty jigs (e.g., for shipment to a single customer). In some variations, the method may include packaging a customized arthroplasty jig in a kit with other components or devices that are used during an arthroplasty procedure.

While the above-described method involves the manufacture of customized arthroplasty jigs having different configurations, in certain variations, a method may include manufacturing two or more arthroplasty jigs having the same configuration. As an example, multiple copies of an arthroplasty jig that has been customized for a particular patient may be manufactured. As another example, in some variations, the above-described apparatus may be used to manufacture one or more non-customized arthroplasty jigs. Advantageously, the apparatus may manufacture these arthroplasty jigs at a relatively high rate. Thus, relatively high volumes of non-customized arthroplasty jigs may be produced in a relatively short period of time.

Figure 6:
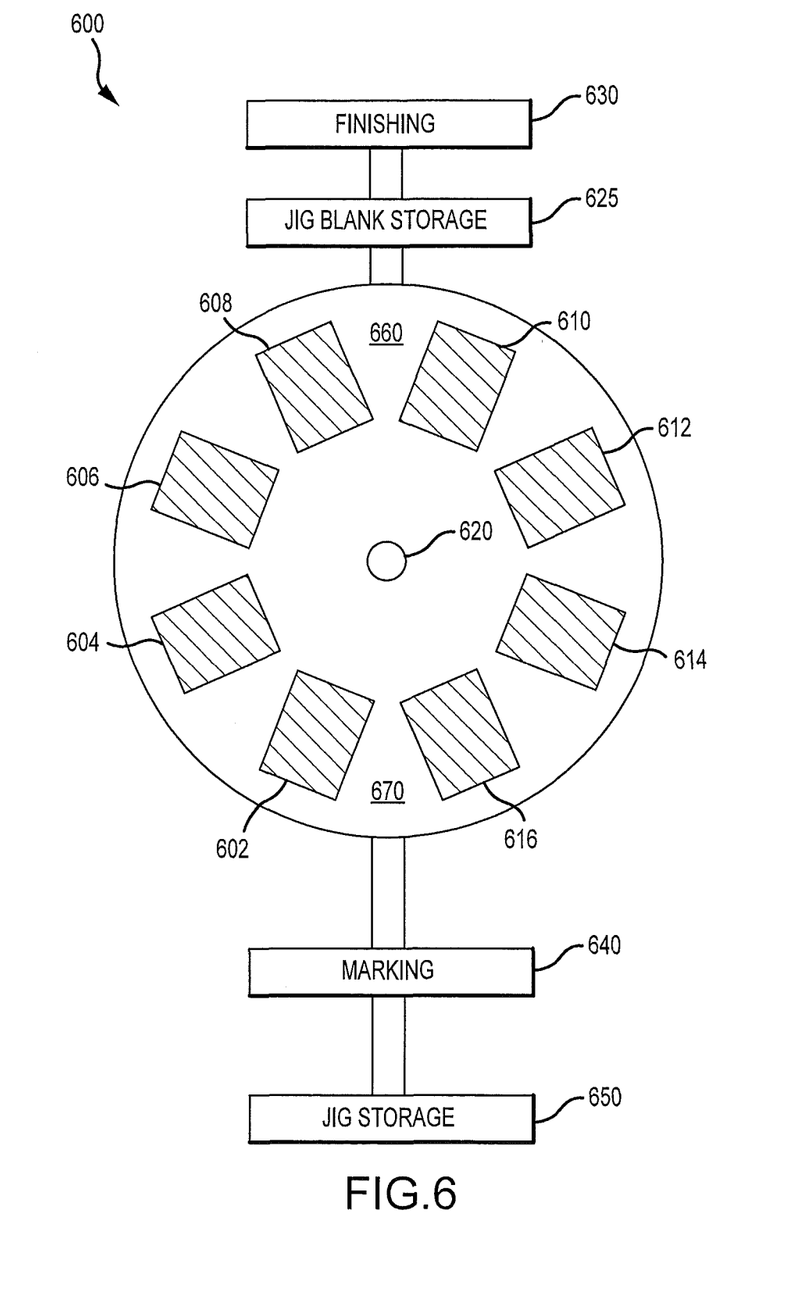
FIG. 6 is an illustration of an apparatus for manufacturing arthroplasty jigs.

FIG. 6 provides a depiction of an apparatus that may be used to perform the method described with reference to FIG. 5. As shown in FIG. 6, an apparatus (600) includes eight rapid production machines (602, 604, 606, 608, 610, 612, 614, and 616) arranged in a generally circular formation, as well as an automated mechanical system (as shown, a robot (620)) that is capable of moving between the different rapid production machines. Apparatus (600) further includes an arthroplasty jig blank storage site (625), a finishing station (630), a marking station (640), and an arthroplasty jig storage site (650).

When apparatus (600) is activated, robot (620) selects an arthroplasty jig blank from arthroplasty jig blank storage site (625). Robot (620) then transports the arthroplasty jig blank to one of the rapid production machines, such as rapid production machine (608). Robot (620), which is in communication with a computer, transmits customized machining instructions from the computer to the rapid production machine so that the rapid production machine will produce a customized arthroplasty jig. The rapid production machine then machines the arthroplasty jig blank to form the customized arthroplasty jig, while robot (620) returns to arthroplasty jig blank storage site (625) to select another arthroplasty jig blank. Robot (620) then transports the other arthroplasty jig blank to another rapid production machine, such as rapid production machine (610), and transmits customized machining instructions from the computer to the rapid production machine. The customized machining instructions that are provided to the first rapid production machine will generally be different from the customized machining instructions that are provided to the second rapid production machine, as the two sets of instructions typically will correspond to different patients' anatomies.

After an arthroplasty jig has been produced, robot (620) retrieves the arthroplasty jig from the rapid production machine that produced it, and transports the arthroplasty jig to finishing station (630). At finishing station (630), the arthroplasty jig can, for example, be cleaned and/or packaged. As an example, the arthroplasty jig may be sterilized and packaged in a protective packaging. Examples of sterilization methods that may be used at the finishing station include chemical sterilization, e-beam sterilization, and gamma ray sterilization. In some variations, an arthroplasty jig may be sterilized by autoclaving. In certain variations, an arthroplasty jig may be sterilized at a different location, either as an alternative to or in addition to being sterilized at the finishing station. For example, an arthroplasty jig may be sterilized at a hospital (e.g., by autoclaving).

Once the arthroplasty jig has completed its time at the finishing station, robot (620) can retrieve the arthroplasty jig and transport it, for example, to marking station (640). At the marking station, the arthroplasty jig and/or any packaging around the arthroplasty jig may be marked or labeled. Examples of information that may be included on the marks or labels include inventory control numbers, manufacture dates, patient data, physician or hospital data, company logos, barcodes, etc. The marking or labeling may be conducted using, for example, laser technology or machine engraving, or simply adhesive stickers that are, for example, applied directly to the arthroplasty jig packaging. After the arthroplasty jig has been marked and/or labeled, robot (620) transports the arthroplasty jig to arthroplasty jig storage site (650), where the arthroplasty jig remains until it is moved elsewhere (e.g., until it is shipped to a customer).

In some variations, the rapid production machines are computer numerical control machines. Other examples of rapid production machines that may be used include stereo-lithograph machines. While apparatus (600) is shown as having eight rapid production machines, an apparatus can have a lower (e.g., two, four, or six) or higher (e.g., ten, twelve, or fourteen) number of rapid production machines. An apparatus may have an even number of rapid production machines, or an odd number of rapid production machines. The rapid production machines may all be of the same type, or may be different from each other. In certain variations, an apparatus may include a rapid production machine having at least two different components that each are configured to form an arthroplasty jig from an arthroplasty jig blank. Thus, the rapid production machine may be used to produce multiple arthroplasty jigs. In some variations, an apparatus may include just one rapid production machine.

Figure 7:
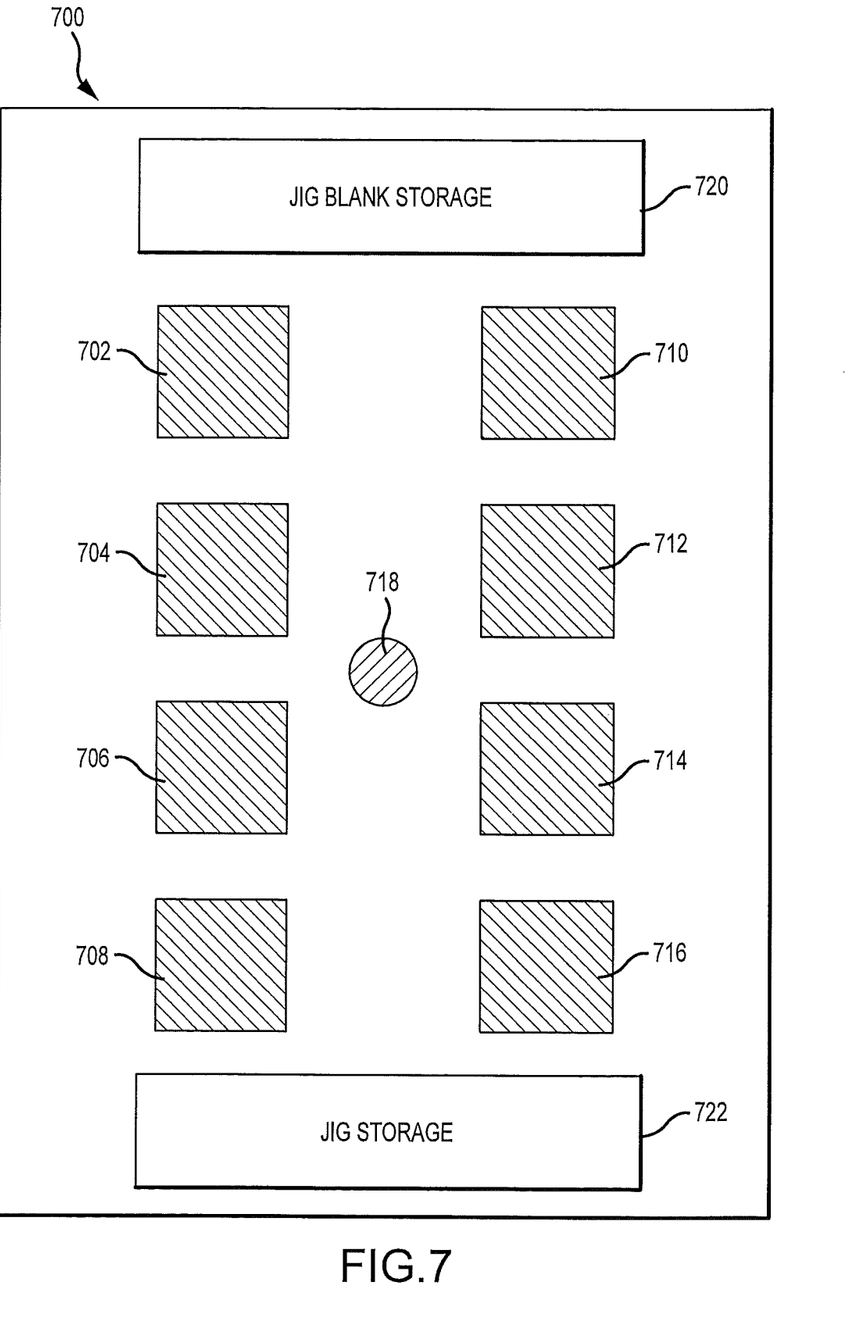
FIG. 7 is an illustration of an apparatus for manufacturing arthroplasty jigs.

While the rapid production machines in apparatus (600) are arranged in a generally circular formation, other formations may be used. As an example, rapid production machines may be arranged in one or more rows, such as two rows, three rows, four rows, five rows, or ten rows. For example, FIG. 7 shows an apparatus (700) including eight rapid production machines (702, 704, 706, 708, 710, 712, 714, and 716) that are arranged in two rows of four rapid production machines each. Apparatus (700) further includes an automated mechanical system (as shown, a robot (718)), an arthroplasty jig blank storage site (720), and an arthroplasty jig storage site (722). The arrangement of the rapid production machines in apparatus (700) may, for example, allow robot (718) to move relatively easily between the arthroplasty jig blank storage site, the various rapid production machines, and the arthroplasty jig storage site.

As further examples, rapid production machines may be arranged in square or oval formations, or may be arranged in other regular formations (such as an X), or in irregular formations. The formation in which the rapid production machines are arranged may be selected, for example, based on the projected path of movement of the automated mechanical system through the apparatus. For example, and referring back to FIG. 6, the rapid production machines of apparatus (600) are arranged to provide a pathway (660) for robot (620) to easily access arthroplasty jig blank storage site (625) and finishing station (630), as well as a pathway (670) for robot (620) to easily access marking station (640) and arthroplasty jig storage site (650). In some variations, the formation in which the rapid production machines are arranged may be selected based on the size and/or configuration of the available manufacturing space.

While the above-described apparatuses include one arthroplasty jig blank storage site and one arthroplasty jig storage site, an apparatus may include multiple storage sites for arthroplasty jig blanks and/or arthroplasty jigs. Similarly, an apparatus may include multiple finishing stations and/or marking stations, or may not include some or all of these sites or stations. The components of an apparatus may be selected according to the particular needs and requirements of the manufacturing process being conducted.

As discussed above, in some variations, an automated mechanical system may be a robot. While a robot that is in communication with one computer has been described, in some variations, a robot or another type of automated mechanical system may be in communication with more than one computer, such as two computers, five computers, or ten computers. In certain variations in which the automated mechanical system is a robot, the robot may be stationary or may, for example, be configured to move along one or more tracks and/or rails. In some variations, the robot may be in the form of an arm with a gripper at its end. The arm may be formed of, for example, two metal bars that are connected together by a movable joint. The gripper may be used to grasp and temporarily hold onto an arthroplasty jig or an arthroplasty jig blank. In certain variations, the gripper may have five or six degrees of freedom. While a gripper has been described, a robot that is appropriate for use in the above-described apparatuses may alternatively or additionally include one or more other features that allow the robot to temporarily hold onto an arthroplasty jig or an arthroplasty jig blank. As an example, a robot may include a component that temporarily holds onto an arthroplasty jig or an arthroplasty jig blank via suction. Examples of robots that are commercially available and that may be used in the above-described apparatuses include robots manufactured by FANUC Robotics (Rochester Hills, Mich.).

In some variations, an apparatus may include multiple automated mechanical systems, such as two, five, or ten automated mechanical systems. The automated mechanical systems may all be the same type of automated mechanical system, or may be different from each other. Furthermore, the automated mechanical systems may all communicate with the same computer, or may communicate with different computers. While robots have been described as examples of automated mechanical systems, other types of automated mechanical systems, such as conveyor belts, may be used in the apparatuses and methods described herein.

The arthroplasty jig blanks and arthroplasty jigs described herein may be formed of any of a number of different materials. They may be formed of just one material, or multiple materials, such as a blend of different materials or layers of different materials. Examples of suitable materials include polymers, metals, ceramics, metal alloys, and combinations thereof. Specific examples of polymers include acetal resins (e.g., Delrin®), polyetheretherketones (PEEK), polycarbonates, polyamides, polyesters, polystyrenes, polyacrylates, vinyl polymers, and polyurethanes. Specific examples of metals and metal alloys include gold, platinum, palladium, stainless steel, cobalt alloys (e.g., Elgiloy®), and nickel-titanium alloys (e.g., Nitinol™). In some variations, the arthroplasty jig blanks may be formed of one or more plastics. In such variations, the arthroplasty jig blanks may be formed, for example, using injection molding technology and/or thermal plastic press forming technology. In certain variations, an arthroplasty jig may be intended to be disposable, while in other variations, an arthroplasty jig may be intended to be reusable. The materials out of which an arthroplasty jig is formed may be selected with these and/or other criteria in mind.

In some variations, an arthroplasty jig may include one or more materials that were not included in the arthroplasty jig blank from which the arthroplasty jig was formed. This may occur, for example, as a result of the arthroplasty jig being processed through the finishing station, where the arthroplasty jig may be coated with a coating material, such as an antibacterial coating material.

The arthroplasty jig blanks that are used in an apparatus may have any of a number of different configurations, sizes, and/or shapes. As an example, some arthroplasty jig blanks may be in the form of blocks of material. As another example, some arthroplasty jig blanks may be designed for use with the left side of a patient's body (e.g., a left knee), while other arthroplasty jig blanks are designed for use with the right side of a patient's body (e.g., the right knee). The arthroplasty jig blanks may have certain of these types of features, or may be relatively feature-less. In certain variations of the methods described here, a computer may provide instructions to an automated mechanical system regarding the configuration, size, and/or shape of arthroplasty jig blank to select to form a particular customized arthroplasty jig.

While arthroplasty jigs having one or two slots have been shown, arthroplasty jigs can have any number of slots, apertures, grooves, and/or ridges. Furthermore, arthroplasty jigs can be configured for use in forming more than one planar surface in a damaged bone region. For example, an arthroplasty jig may be used to form two or three planar surfaces in a damaged bone region. The multiple planar surfaces may correspond to multiple planar surfaces in an implant that is to be inserted into the damaged bone region. Moreover, the slots, apertures, grooves, and/or ridges may be used for other purposes besides the aforementioned cutting, drilling, reaming, and resurfacing. For example, apertures in an arthroplasty jig may be used to help position one or more pins that can, for example, be used to secure an implant to a target location.

While methods and apparatuses described herein have been described with respect to the manufacture of arthroplasty jigs, some variations of methods and apparatuses may be used to manufacture implants, such as arthroplasty implants. The implants may, for example, be customized to correspond to particular patients' anatomies. Moreover, while arthroplasty procedures have been described, the jigs and implants described herein may be used in any of a number of different procedures, including, for example, spinal surgery.

In some variations, a manufacturing process may include the use of multiple apparatuses, such as five or ten apparatuses. The apparatuses may operate in conjunction to produce a relatively high output of jigs and/or implants over a relatively short period of time. In certain variations, one apparatus may be configured to manufacture one type of jig or implant, while another apparatus may be configured to manufacture another type of jig or implant. As an example, one apparatus may be configured to manufacture arthroplasty jigs for one customer, while another apparatus is configured to manufacture arthroplasty jigs for a different customer. As another example, one apparatus may be configured to manufacture arthroplasty jigs for left knees, while another apparatus is configured to manufacture arthroplasty jigs for right knees. As an additional example, one apparatus may be configured to manufacture arthroplasty jigs, while another apparatus is configured to manufacture arthroplasty implants.

Furthermore, while one method of manufacturing a customized arthroplasty jig has been described above, other methods may be used. For example, one-, two-, and three-dimensional measurements of a target site may be taken using lasers, electromagnetic or optical tracking systems, or other imaging methods. As an example, while CT and MRI have been described, other imaging methods that may be used include X-ray technology, optical coherence tomography, ultrasound imaging, and optical imaging. In some variations, multiple imaging techniques may be used together to image a target site. Moreover, the measurements that are used to image an area may be taken in a non-invasive manner, or may be taken intra-operatively (e.g., using optical, mechanical, and/or ultrasound probes).

While the methods, devices, and apparatuses have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the pending claims.

The invention claimed is:

1. An apparatus configured for the production of a plurality of customized arthroplasty jigs, the apparatus comprising: a plurality of rapid production machines; and an automated mechanical system that is configured to transport a first arthroplasty jig blank to a first rapid production machine and a second arthroplasty jig blank to a second rapid production machine, wherein the first rapid production machine is configured to form a first arthroplasty jig from the first arthroplasty jig blank and the second rapid production machine is configured to form a second arthroplasty jig from the second arthroplasty jig blank, and the first and second arthroplasty jigs have different configurations.

2. The apparatus of claim 1, wherein the automated mechanical system comprises a robot.

3. The apparatus of claim 1, wherein at least one of the first and second arthroplasty jig blanks is in the form of a block of material.

4. The apparatus of claim 1, wherein the rapid production machines comprise computer numerical control machines.

5. The apparatus of claim 1, wherein the apparatus comprises eight rapid production machines.

6. The apparatus of claim 1, wherein the automated mechanical system is in communication with a computer.

7. The apparatus of claim 6, wherein the computer is configured to provide the automated mechanical system with first machining instructions for forming the first arthroplasty jig.

8. The apparatus of claim 7, wherein the computer is configured to provide the automated mechanical system with second machining instructions for forming the second arthroplasty jig.

9. The apparatus of claim 8, wherein the automated mechanical system is configured to communicate the first machining instructions to the first rapid production machine.

10. The apparatus of claim 9, wherein the automated mechanical system is configured to communicate the second machining instructions to the second rapid production machine.

11. The apparatus of claim 1, wherein the apparatus is configured to produce at least 30 customized arthroplasty jigs per hour.

12. The apparatus of claim 1, wherein the rapid production machines are arranged in rows.

13. The apparatus of claim 1, wherein the rapid production machines are arranged in a circle.

14. The apparatus of claim 1, wherein the automated mechanical system is configured to remove the first arthroplasty jig from the first rapid production machine when formation of the first arthroplasty jig has been completed.

15. The apparatus of claim 14, wherein the automated mechanical system is configured to transport the first arthroplasty jig from the first rapid production machine to a station that is configured to clean arthroplasty jigs.

16. The apparatus of claim 15, wherein the station also is configured to package the arthroplasty jigs after they have been cleaned.

17. The apparatus of claim 14, wherein the automated mechanical system is configured to transport the second arthroplasty jig from the second rapid production machine when formation of the second arthroplasty jig has been completed.

18. An apparatus configured for the production of a plurality of customized arthroplasty jigs, the apparatus comprising: a rapid production machine comprising a first component and a second component; and an automated mechanical system that is configured to transport a first arthroplasty jig blank to the first component and a second arthroplasty jig blank to the second component, wherein the first component is configured to form a first arthroplasty jig from the first arthroplasty jig blank and the second component is configured to form a second arthroplasty jig from the second arthroplasty jig blank, and the first and second arthroplasty jigs have different configurations.

19. The apparatus of claim 18, wherein the automated mechanical system comprises a robot.

20. The apparatus of claim 18, wherein the rapid production machine comprises a computer numerical control machine.

21. The apparatus of claim 18, wherein the automated mechanical system is in communication with a computer.

22. The apparatus of claim 21, wherein the computer is configured to provide the automated mechanical system with first machining instructions for forming the first arthroplasty jig.

23. The apparatus of claim 22, wherein the computer is configured to provide the automated mechanical system with second machining instructions for forming the second arthroplasty jig.

24. The apparatus of claim 23, wherein the automated mechanical system is configured to communicate the first machining instructions to the first component of the rapid production machine.

25. The apparatus of claim 24, wherein the automated mechanical system is configured to communicate the second machining instructions to the second component of the rapid production machine.

26. The apparatus of claim 18, wherein the apparatus is configured to produce at least 30 customized arthroplasty jigs per hour.

* * * * *